US011642401B2

(12) United States Patent
Masopust, Jr. et al.

(10) Patent No.: US 11,642,401 B2
(45) Date of Patent: May 9, 2023

(54) ACTIVATION OF RESIDENT MEMORY T CELLS FOR CANCER IMMUNOTHERAPY

(71) Applicant: Regents of the University of Minnesota, Minneapolis, MN (US)

(72) Inventors: David B. Masopust, Jr., Minneapolis, MN (US); Vaiva D. Vezys, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 95 days.

(21) Appl. No.: 16/939,962

(22) Filed: Jul. 27, 2020

(65) Prior Publication Data

US 2021/0000935 A1 Jan. 7, 2021

Related U.S. Application Data

(63) Continuation of application No. 15/774,163, filed as application No. PCT/US2016/060834 on Nov. 7, 2016, now Pat. No. 10,722,537.

(60) Provisional application No. 62/252,328, filed on Nov. 6, 2015.

(51) Int. Cl.
*A61K 39/00* (2006.01)
*A61K 35/17* (2015.01)
*A61K 39/395* (2006.01)
*A61K 35/12* (2015.01)
*A61K 48/00* (2006.01)
*C12N 5/0783* (2010.01)

(52) U.S. Cl.
CPC .......... *A61K 39/0011* (2013.01); *A61K 35/17* (2013.01); *A61K 39/395* (2013.01); *A61K 39/39558* (2013.01); *A61K 48/0058* (2013.01); *A61K 48/0066* (2013.01); *A61K 2039/585* (2013.01); *C12N 5/0636* (2013.01); *C12N 2710/10032* (2013.01); *C12N 2760/10034* (2013.01); *C12N 2760/20234* (2013.01); *Y02A 50/30* (2018.01)

(58) Field of Classification Search
CPC ..... A61P 35/00; A61K 35/17; A61K 2300/00; A61K 2039/5156; Y02A 50/30
See application file for complete search history.

(56) References Cited

U.S. PATENT DOCUMENTS

| 10,722,537 | B2 | 7/2020 | Masopust, Jr. et al. |
|---|---|---|---|
| 2006/0120995 | A1 | 6/2006 | Shah |
| 2009/0130144 | A1 | 5/2009 | Strome et al. |
| 2012/0020998 | A1 | 1/2012 | Plumas et al. |
| 2016/0199479 | A1 | 7/2016 | Su et al. |
| 2018/0325952 | A1 | 11/2018 | Masopust, Jr. et al. |
| 2021/0093713 | A1 | 4/2021 | Masopust, Jr. et al. |

FOREIGN PATENT DOCUMENTS

| WO | WO 2012/123755 | | 9/2012 |
|---|---|---|---|
| WO | WO 2015/069770 | | 5/2015 |
| WO | WO 2015/123496 | | 8/2015 |
| WO | WO2015123496 | * | 8/2015 |
| WO | WO 2017/079747 | | 5/2017 |
| WO | WO2017079747 | * | 5/2017 |
| WO | WO 2017/112830 | | 6/2017 |
| WO | WO 2017/177204 | | 10/2017 |

OTHER PUBLICATIONS

Beckhove et al., "Specifically activated memory T cell subsets from cancer patients recognize and reject xenotrausplanted autologous tumors," J. Clin. Invest., 114(1):67-76, Jul. 2004.
Casey et al., "Antigen-independent differentiation and maintenance of effector-like resident memory T cells in tissues," J. Immunol., 188(10):4866-75, May 2012.
Davies et al., "Capturing complex tumour biology in vitro: histological and molecular characterisation of precision cut slices," Sci. Reports, Dec. 9, 2015, 5:17187, 17 pages.
Erkes et al., "Virus-Specific CD8+ T Cells Infiltrate Melanoma Lesions and Retain Function Independently of PD-1 Expression," J. Immnol., 198:2979-2988, Feb. 2017.
Kim et al., "HISAT: a fast spliced aligner with low memory requirements," Nat. Methods, 12(4):357-60, Apr. 2015.
Kohlhapp et al., "NK cells and CD8+ T cells cooperate to improve therapeutic responses in melanoma treated with interleukin-2 (IL-2) and CTLA-4 blockade," J. Immunother., 3(18):1-13, May 2015.
LabCorp.com [online], "Patient Test Information: HLA Testing," available no later than Aug. 3, 2017, retrieved on Aug. 31, 2020, retrieved from URL<labcorp.com/help/patient-test-mfo/hl-testing>, 7 pages.
Love et al., "Moderated estimation of fold change and dispersion for RNA-seq data with DESeq2," Genome Biol., 15:550, Dec. 2014.
Masopust et al., "Dynamic T cell migration program provides resident memory within intestinal epithelium," J. Exp. Med., 207(3):553-64, Mar. 2010.
Millar et al., "Antibody-mediated delivery of viral epitopes to tumors harnesses CMV-specific T cells for cancer therapy," Nature Biotechnology, Feb. 2020, 38(4):420-425.
Nishio et al., "Armed oncolytic virus enhances immune functions of chimeric antigen receptor-modified T cells in solid tumors," cancer research, 74(18):5195-205, Jul. 2014.
Pauken et al., "Cutting edge: identification of autoreactive CD4+ and CD8+ T cell subsets resistant to PD-1 pathway blockade," J. Immunol., 194(8):3551-3555, Apr. 2015.
PCT International Preliminary Report on Patentabilty in International Appln. No. PCT/US2016/060834, dated May 8, 2018, 6 pages.
PCT International Preliminary Report on Patentabilty in International Appln. No. PCT/US2018/045244, dated Mar. 10, 2020, 10 pages.
PCT International Search Report and Written Opinion in International Appln. No. PCT/US2016/060834 dated Jan. 24, 2017, 7 pages.

(Continued)

*Primary Examiner* — Barry A Chestnut
(74) *Attorney, Agent, or Firm* — Fish & Richardson P.C.

(57) ABSTRACT

Provided herein are methods of treating cancer by activating resident memory T cells using one or more antigenic peptides.

22 Claims, 14 Drawing Sheets

(56) References Cited

OTHER PUBLICATIONS

PCT International Search Report and Written Opinion in International Appln. No. PCT/US2018/045244, dated Dec. 21, 2018, 10 pages.
Schenkel et al., "Resident memory CD8 T cells trigger protective innate and adaptive immune responses," Science, 346(6205):98-101, Oct. 2014.
Schenkel et al., "Sensing and alarm function of resident memory $CD8^+$ T cells," Nat. Immunol., 14(5):509-14, May 2013.
Simoni et al., "Bystander CD8+ T cells are abundant and phenotypically distinct in human tumour infiltrates," Nat., 557:575-579, May 2018.
Steinert et al., "Quantifying memory CD8 T cells reveals regionalization of immunosurveillance," Cell, 161(4):737-49, May 2015.
Wang et al., "Manufacture of tumor-and virus-specific T lymphocytes for adoptive cell therapies," Cancer Gene Therapy, 22(2):85, Feb. 2015.
U.S. Appl. No. 16/635,205, filed Jan. 30, 2020, David B. Masopust Jr., Published.
Fujita Y, Taguchi H. Current status of multiple antigen-presenting peptide vaccine systems: Application of organic and inorganic nanoparticles. Chem Cent J. 2011;5(1):48. Published Aug. 23, 2011. doi:10.1186/1752-153X-5-48 (Year: 2011).
Lanitis E, Irving M, Coukos G. Targeting the tumor vasculature to enhance T cell activity. Curr Opin Immunol. Apr. 2015; 33:55-63. doi: 10.1016/j.coi.2015.01.011. Epub Feb. 6, 2015. PMID: 25665467; PMCID: PMC4896929. (Year: 2015).
Sawada Y, Yoshikawa T, Shimomura M, Iwama T, Endo I and Nakatsura T: Programmed death-1 blockade enhances the antitumor effects of peptide vaccine-induced peptide-specific cytotoxic T lymphocytes. Int J Oncol 46: 28-36, 2015 (Year: 2014).
Von Eichborn, J., Woelke, A.L., Castiglione, F. et al. VaccImm: simulating peptide vaccination in cancer therapy. BMC Bioinformatics 14, 127 (2013). https://doi.org/10.1186/1471-2105-14-127(Year: 2013).

\* cited by examiner

DAPI OT-I  DAPI

ACTIVATION OF RESIDENT MEMORY T CELLS FOR CANCER IMMUNOTHERAPY

CROSS REFERENCE TO RELATED APPLICATIONS

This application is a continuation application of U.S. patent application Ser. No. 15/774,163, filed May 7, 2018, which is a National Stage application under 35 U.S.C. § 371 of International Application No. PCT/US2016/060834 having an International Filing Date of Nov. 7, 2016, which claims the benefit of U.S. Patent Application No. 62/252,328, filed on Nov. 6, 2015, which are incorporated herein by reference.

FEDERALLY SPONSORED RESEARCH OR DEVELOPMENT

This invention was made with government support under AI084913 awarded by National Institutes of Health. The government has certain rights in the invention.

TECHNICAL FIELD

This disclosure generally relates to immunology and immunotherapy.

BACKGROUND

Current data supports a model by which early effector CD8 T cells migrate into non-lymphoid tissue, differentiate into long-lived memory CD8 T cells, and remain resident without recirculating. Methods are described herein whereby certain resident memory T cells are reactivated for therapeutic purposes.

SUMMARY

In one aspect, a method of increasing the efficacy of immunotherapy in an individual is provided. Such a method typically includes administering an adjuvant to a solid tumor, wherein the adjuvant comprises at least one antigenic peptide.

Immunotherapy includes, without limitation, therapy with CAR T cells, adoptive cell therapy, and/or checkpoint blockade therapy. In some embodiments, the adjuvant is administered prior to the immunotherapy. In some embodiments, the adjuvant is administered with the immunotherapy. In some embodiments, the adjuvant is administered after the immunotherapy.

In some embodiments, the administering step comprises injecting the adjuvant into the solid tumor. In some embodiments, the administering step comprises topically applying the adjuvant to the solid tumor or to an area adjacent or near the solid tumor.

In some embodiments, the adjuvant comprises at least two antigenic peptides (e.g., at least five antigenic peptides, at least ten antigenic peptides, at least twenty antigenic peptides). In some embodiments, the adjuvant includes at least one antigenic peptide from a virus or a bacteria. Representative viruses include, without limitation, an influenza virus, a cold virus, an adenovirus, an adeno-associated virus, a cytomegalovirus (CMV), a measles virus (e.g., rubeola), an Epstein-Barr virus, human papillomavirus (HPV), a norovirus, a polyoma virus, a hepatitis A, B and/or C virus, a Zika virus, a respiratory syncytial virus (RSV), or a herpes simplex virus (HSV). Representative bacteria include, without limitation, *Escherichia coli*, *Salmonella*, *Helicobacter pylori*, *Staphylococcus aureus*, *Streptococcal* spp., or *Campylobacter* spp. In some embodiments, the adjuvant includes at least one antigenic peptide from a vaccine. Representative vaccines include, without limitation, a chickenpox vaccine, a polio vaccine, a German measles vaccine, a mumps vaccine, a Diphtheria vaccine, and a tetanus vaccine.

In some embodiments, the adjuvant includes at least two antigenic peptides from a first microorganism, at least two antigenic peptides from a second microorganism and at least two antigenic peptides from a third microorganism. In some embodiments, the adjuvant includes at least three antigenic peptides from a first microorganism, at least three antigenic peptides from a second microorganism and at least three antigenic peptides from a third microorganism. In some embodiments, the first microorganism is EBV, wherein the second microorganism is CMV, and wherein the third microorganism is influenza.

In some embodiments, such a method can further include determining the major histocompatibility complex (MHC) genotype of the individual.

In some embodiments, such a method can further include monitoring at least one of the following or at least two of the following or at least three of the following: size of the solid tumor; presence and/or amount of one or more chemokines (e.g., CXCL9, CXCL10, fractalkine, CCL2, CCL3/4, CCLS); presence and/or amount of leukocytes (e.g., inflammatory monocytes, B cells); presence and/or amount of serum antibodies; presence and/or amount of a cancer immunotherapeutic (e.g., CAR-T cells) associated with or in the vicinity of the solid tumor; activation of local dendritic cells; activation of NK cells; and/or up-regulation of vascular adhesion molecules (e.g., VCAM-1).

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Figure 1:
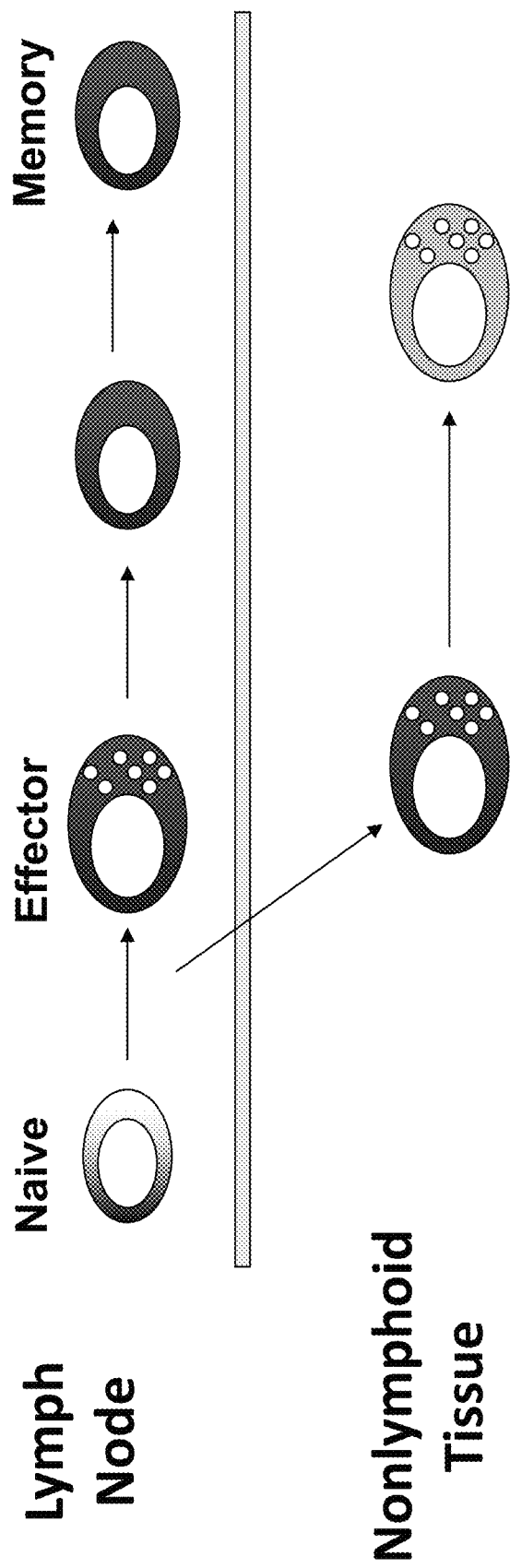
FIG. 1 is a schematic that shows the pathway to resident memory T cells ($T_{RM}$).

The functions of $T_{RM}$ can be leveraged for therapeutic purposes as described here. The methods described herein exploit pre-existing resident memory T cells ($T_{RM}$). Specifically, the methods described herein co-opt the natural "sensing and alarm" function of $T_{RM}$ and utilizes it to target immune responses and therapies to tumors. For example, specific peptides can be used to recruit T cells and antibodies to the site of a tumor and to promote an immunostimulatory and effector environment. In addition, local reactivation of $T_{RM}$ cells originally established against, for example, a particular pathogen, can be achieved using one or more peptides that are unrelated to the particular pathogen to increase local immunity. The results described herein demonstrate how reactivation of a relatively small numbers of $T_{RM}$ cells using peptides can result in a signal that is amplified to more abundant members of the innate immune system in order to trigger an organ-wide immunological response.

The methods described herein can be used to increase the efficacy of immunotherapy by reactivating $T_{RM}$ in an individual. Such methods can include administering an adjuvant to a tumor (e.g., a solid tumor), typically in conjunction with one or more forms of immunotherapy. In essence, peptides that reactivate patients' pre-existing $T_{RM}$, can be used as a potent local adjuvant. Cancer immunotherapies are known in the art and include, without limitation, the administration of CAR-T cells, checkpoint blockade therapy (e.g., KEYTRUDA, OPDIVO, YERVOY), or other adoptive cell therapies for virtually any disease. The methods described herein solve several of the problems currently encountered when delivering immunotherapies, including targeting of the immunotherapy (e.g., chimeric antigen receptor (CAR)-T cells) to the site of a tumor, concentration of checkpoint blockade antibodies at the site of a tumor, activation of the innate immune system at the site of a tumor, and enhancing activation of the adaptive immune response against tumors.

$T_{RM}$ stimulation as described herein can augment and extend the range of current cancer immunotherapies by, for example, increasing the ability of appropriate CAR-T cell therapies to target solid tumors, reducing the amount of checkpoint blockade antibodies required for therapy, as these antibodies have toxic off-target effects, promoting systemic anti-tumor immune responses, and increasing the immunostimulatory environment within tumors for eradication of cancer by the immune system. Since $T_{RM}$ stimulation controls local immune system activation and recruitment, the methods described herein can be applied to any number of solid tumors (e.g., brain, skin, ovarian, breast, gastrointestinal and lung tumors, neuroblastomas, Wilms tumors, rhabdomyosarcomas, retinoblastomas, osteosarcomas, Ewing sarcomas, Kaposi sarcoma) as well as a range of diseases in addition to tumors including, without limitation, autoimmune disease (e.g., arthritis, IBD, psoriasis, multiple sclerosis), hepatitis C virus, parasite infection, tuberculosis, allergies, and atopy.

As used herein, an adjuvant includes one or more antigenic peptides that, when administered to a tumor (e.g., a solid tumor), activate the resident memory T cells that reside therein. An antigenic peptide, also referred to as an immunogenic peptide, is understood in the art to refer to a peptide that produces, or results in, an antigen-specific stimulation of T cells. As used herein, an antigenic peptide is a peptide from any microorganism with which the individual has previously been infected and to which the individual has previously developed an immune response against. The infection can be a result of a previous infection or exposure via a vaccine. Simply by way of example, the source of an antigenic peptide can be, without limitation, a virus against which the individual has developed an immune response (e.g., an influenza virus, a cold virus, an adenovirus, an adeno-associated virus, a cytomegalovirus (CMV), a measles virus (e.g., rubeola), an Epstein-Barr virus, human papillomavirus (HPV), a norovirus, a polyoma virus, a hepatitis A, B and/or C virus, a Zika virus, a respiratory syncytial virus (RSV), or a herpes simplex virus (HSV)), a bacteria against which the individual has developed an immune response (e.g., *Escherichia coli*, *Salmonella*, *Helicobacter pylori*, *Staphylococcus aureus*, *Streptococcal* spp., or *Campylobacter* spp.), or a vaccine with which the individual has been inoculated (against, e.g., chickenpox (i.e., varicella-zoster virus (VZV)), polio, German measles (*Rubella* spp.), mumps, Diphtheria, or tetanus (i.e., *Clostridium tetani*)).

It would be understood that a combination or mixture of antigenic peptides (e.g., a "cocktail" of antigenic peptides) can be used to activate a plurality of different antigen-specific T cells (i.e., T cells specific to a plurality of antigens), thereby increasing the likelihood and potency of an immune response. For example, an adjuvant as described herein can include at least two antigenic peptides (e.g., at least five antigenic peptides, at least ten antigenic peptides, or at least twenty antigenic peptides). Notably, the methods described herein require nothing more than one or more antigenic peptides to stimulate the immune system, i.e., no microbial products or other adjuvants, including alum or Toll-like receptor agonists, are required.

Antigenic peptides from a number of microorganisms (e.g., infectious diseases) are known in the art. For example, and without limitation, antigenic peptides can be one or more antigenic peptides from CMV (see, e.g., Cat. No. PM-C-HCMV-1 from JPT Peptide Technologies), EBV (see, e.g., Cat. Nos. PM-EBV-EBNA1, PM-EBV-EBNA2, PM-EBV-EBNA3a, etc. from JPT Peptide Technologies), HPV (see, e.g., Cat. No. PM-HPV16-E6 from JPT Peptide Technologies), Influenza A (e.g., Cat. Nos. PM-INFA-HA-Cal or PM-INFA_MP1 from JPT Peptide Technologies), VZV (see, e.g., Cat. No. PM-VZV-gE from JPT Peptide Technologies), and combinations thereof. Antigenic peptides for use in the methods described herein can be one or more peptides selected from defined HLA class I-restricted T cell epitopes (e.g., Cat. No. PM-CEF-E-2 from JPT Peptide Technologies). In addition, methods of screening and identifying antigenic polypeptides also are well known in the art.

An adjuvant as used herein can include multiple antigenic peptides from a multitude of microorganisms. For example, an adjuvant can include at least two antigenic peptides (e.g., at least three antigenic peptides, at least four antigenic peptides, etc.) from at least two microorganisms (e.g., at least three microorganisms, at least four microorganisms, at least five microorganisms, etc.). Simply by way of example, in one embodiment, an adjuvant includes two or three antigenic peptides from each of two or three different microorganisms. For example, an adjuvant can include three different antigenic peptides from each of EBV, CMV, and influenza.

Peptides are known in the art and generally refer to chains of amino acids linked by amide (or peptide) bonds. Peptides sometimes are defined as being less than about 50 amino acids in length (e.g., about 5 to about 50 amino acids, about 5 to about 45 amino acids, about 8 to about 45 amino acids, about 10 to about 40 amino acids, about 15 to about 35 amino acids, about 20 to about 30 amino acids, about 20 to about 50 amino acids, or about 25 to about 50 amino acids in length) but, as used herein, peptides can be longer than 50 amino acids in length (e.g., up to about 55 amino acids, up to about 60 amino acids, up to about 70 amino acids, up to about 80 amino acids, up to about 90 amino acids, or up to about 100 amino acids). Peptides as used herein (e.g., antigenic peptides) generally contain naturally occurring amino acids, but can include non-naturally occurring amino acids to the extent that recognition of the antigenic peptide by T cells (e.g., $T_{RM}$ cells) is not impeded or disrupted.

The term "purified" as used herein with respect to a peptide refers to a peptide that has been separated or purified from cellular components that naturally accompany it. Typically, the peptide is considered "purified" when it is at least 70% (e.g., at least 75%, 80%, 85%, 90%, 95%, or 99%) by dry weight, free from the proteins and naturally occurring molecules with which it is naturally associated. Since a peptide that is chemically synthesized is, by nature, separated from the components that naturally accompany it, a synthetic peptide is "purified." Peptides can be obtained (e.g., purified) from natural sources (e.g., a biological sample) by known methods such as DEAE ion exchange, gel filtration, and hydroxyapatite chromatography. A purified peptide also can be obtained, for example, by expressing a nucleic acid in an expression vector. In addition, a purified peptide can be obtained by chemical synthesis. The extent of purity of a peptide can be measured using any appropriate method, e.g., column chromatography, polyacrylamide gel electrophoresis, or HPLC analysis.

In some instances, it may be desirable to determine the major histocompatibility complex (MHC) genotype of the individual prior to administering any antigenic peptides to ensure the correct, appropriate or optimized cocktail of antigenic peptides is administered. Methods of determining the MHC genotype of an individual are known in the art and include, for example, screening blood with a panel of peptides to identify those peptides to which T cells in the blood sample respond. T cell response to a particular peptide can be determined using any number of methods including, without limitation, MHC-based class I staining or cytokine (e.g., interferon-gamma) production.

An adjuvant as described herein can be administered to an individual at any time relative to the delivery of the immunotherapy. For example, an adjuvant as described herein can be administered with the immunotherapy. The adjuvant described herein can be combined with the immunotherapeutic composition and administered together or the adjuvant described herein can be administered separately but concurrently, or essentially concurrently, with the immunotherapeutic composition. In addition, an adjuvant as described herein can be administered to an individual before delivery of the immunotherapy (e.g., one to eight hours, one to four days or one week prior to administration of the immunotherapeutic agent), after delivery of the immunotherapy (e.g., one to eight hours, one to four days or one week after administration of the immunotherapeutic agent), or any combination thereof.

As described herein, reactivation of $T_{RM}$ in an individual can be monitored using any of a number of biological factors. For example, a skilled artisan would appreciate that the size of the tumor can be monitored (e.g., before, during and/or following immunotherapy with an adjuvant as described herein) and/or the presence or amount of a cancer immunotherapeutic (e.g., CAR-T cells) can be monitored. Additionally or alternatively, the presence and/or amount of one or more chemokines (e.g., CXCL9, CXCL10, fractalkine, CCL2, CCL3/4, CCL5), one or more leukocytes (e.g., inflammatory monocytes, T cells, B cells) and/or one or more serum antibodies can be monitored as an indicator of the effectiveness or efficacy of the immunotherapy. Additionally or alternatively, the activation of local dendritic cells, the activation of NK cells, and/or the up-regulation of vascular adhesion molecules (e.g., VCAM-1) can be monitored as an indicator of the effectiveness or efficacy of the immunotherapy.

In addition to at least one antigenic peptide, an adjuvant as used herein typically includes a pharmaceutically acceptable carrier. Pharmaceutically acceptable carriers are well known in the art. See, for example *Remington: The Science and Practice of Pharmacy*, University of the Sciences in Philadelphia, Ed., 21$^{st}$ Edition, 2005, Lippincott Williams & Wilkins; and *The Pharmacological Basis of Therapeutics*, Goodman and Gilman, Eds., 12$^{th}$ Ed., 2001, McGraw-Hill Co. The type of pharmaceutically acceptable carrier used in a particular formulation can depend on various factors, such as, for example, the physical and chemical properties of the compound, the route of administration, and the manufacturing procedure. Pharmaceutically acceptable carriers are available in the art, and include those listed in various pharmacopoeias. See, for example, the U.S. Pharmacopeia (USP), Japanese Pharmacopoeia (JP), European Pharmacopoeia (EP), and British pharmacopeia (BP); the U.S. Food and Drug Administration (FDA) Center for Drug Evaluation and Research (CDER) publications (e.g., Inactive Ingredient Guide (1996)); and Ash and Ash, Eds. (2002) Handbook of Pharmaceutical Additives, Synapse Information Resources, Inc., Endicott, N.Y.

As used herein, "pharmaceutically acceptable carrier" is intended to include any and all excipients, solvents, dispersion media, coatings, antibacterial and anti-fungal agents, isotonic and absorption delaying agents, and the like, compatible with administration. The use of such media and agents for pharmaceutically acceptable carriers is well known in the art. Except insofar as any conventional media or agent is incompatible with a compound, use thereof is contemplated.

An adjuvant as described herein can be formulated for parenteral administration (e.g., by injection). Such formulations are usually sterile and, can be provided in unit dosage forms, e.g., in ampoules, syringes, injection pens, or in multi-dose containers, the latter usually containing a preservative. The formulations may take such forms as suspensions, solutions, or emulsions in oily or aqueous vehicles (e.g., saline), and may contain other agents, such as buffers, tonicity agents, viscosity enhancing agents, surfactants, suspending and dispersing agents, antioxidants, biocompatible polymers, chelating agents, and preservatives. Depending on the injection site, the vehicle may contain water, saline, a synthetic or vegetable oil, and/or organic co-solvents. In certain instances, such as with a lyophilized product or a concentrate, the parenteral formulation would be reconstituted or diluted prior to administration. Polymers such as poly(lactic acid), poly(glycolic acid), or copolymers thereof, can serve as controlled or sustained release matrices, in addition to others well known in the art.

An adjuvant as described herein can be formulated for topical administration, such as through a skin patch, a semi-solid, or a liquid formulation, for example a gel, a (micro-) emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and the use of complexing agents.

This disclosure also provides for articles of manufacture that include a composition as described herein (e.g., one or more antigenic peptides and a pharmaceutically acceptable carrier). An article of manufacture can include a composition packaged with suitable packaging materials. Articles of manufacture also can include means for introducing the composition to the site of a tumor. Means for introducing the composition to the site of a tumor include syringes and injection pens.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Pathway to Residency

FIG. 1 is a schematic that shows the pathway to resident memory T cells ($T_{RM}$). T cell migration is dependent on the differentiation state of the T cells. For example, memory T cells do not recirculate between blood and many non-lymphoid tissues. Thus, many tissues are not surveyed by T cells that are recirculating through the blood or are injected into the blood. However, shortly after priming (i.e., the original activation of a T cell by an antigen), effector T cells appear to have a window of opportunity to enter non-lymphoid tissue, after which they differentiate in situ into a resident memory T cell ($T_{RM}$) that no longer recirculates. These $T_{RM}$ become "parked" within the tissue. This phenomenon is described in more detail in, for example, Masopust et al. (2010, J. Exp. Med., 207(3):553-64) and Steiner et al. (2015, Cell, 161(4):737-49).

Example 2—Effects of Environment on Residency

Figure 2:
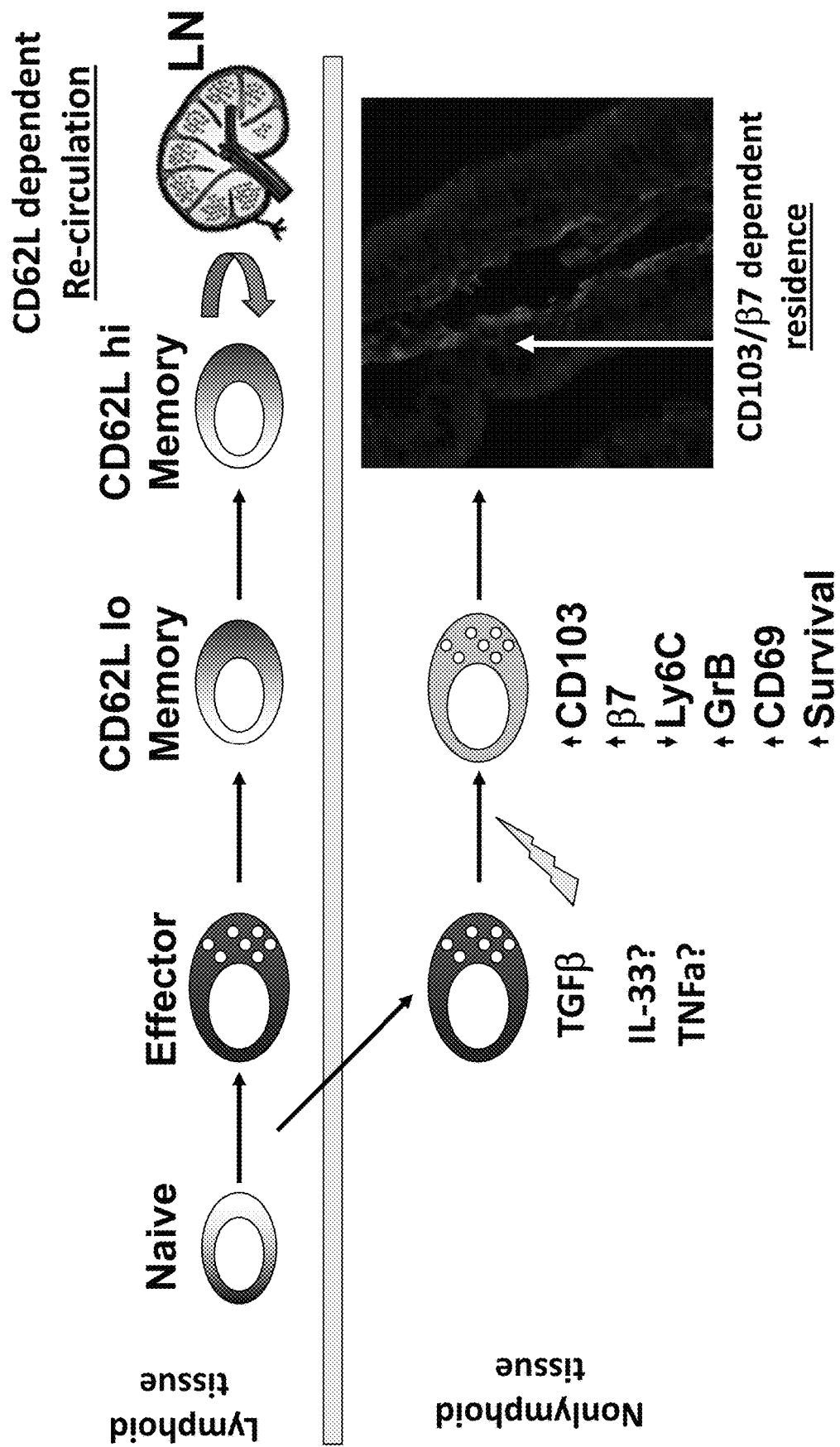
FIG. 2 is a schematic showing how the environmental milieu induces a $T_{RM}$ differentiation program.

FIG. 2 is a schematic showing how the environmental milieu induces a $T_{RM}$ differentiation program. When $T_{RM}$ precursor cells come into contact with non-lymphoid tissues, they receive signals from the local tissue microenvironment that guide and shape $T_{RM}$ differentiation. Thus, the differentiation state of $T_{RM}$ is regulated by its anatomical location. This phenomenon is described in more detail in, for example, Casey et al. (2012, J. Immunol., 188:4866-75).

Figure 3:
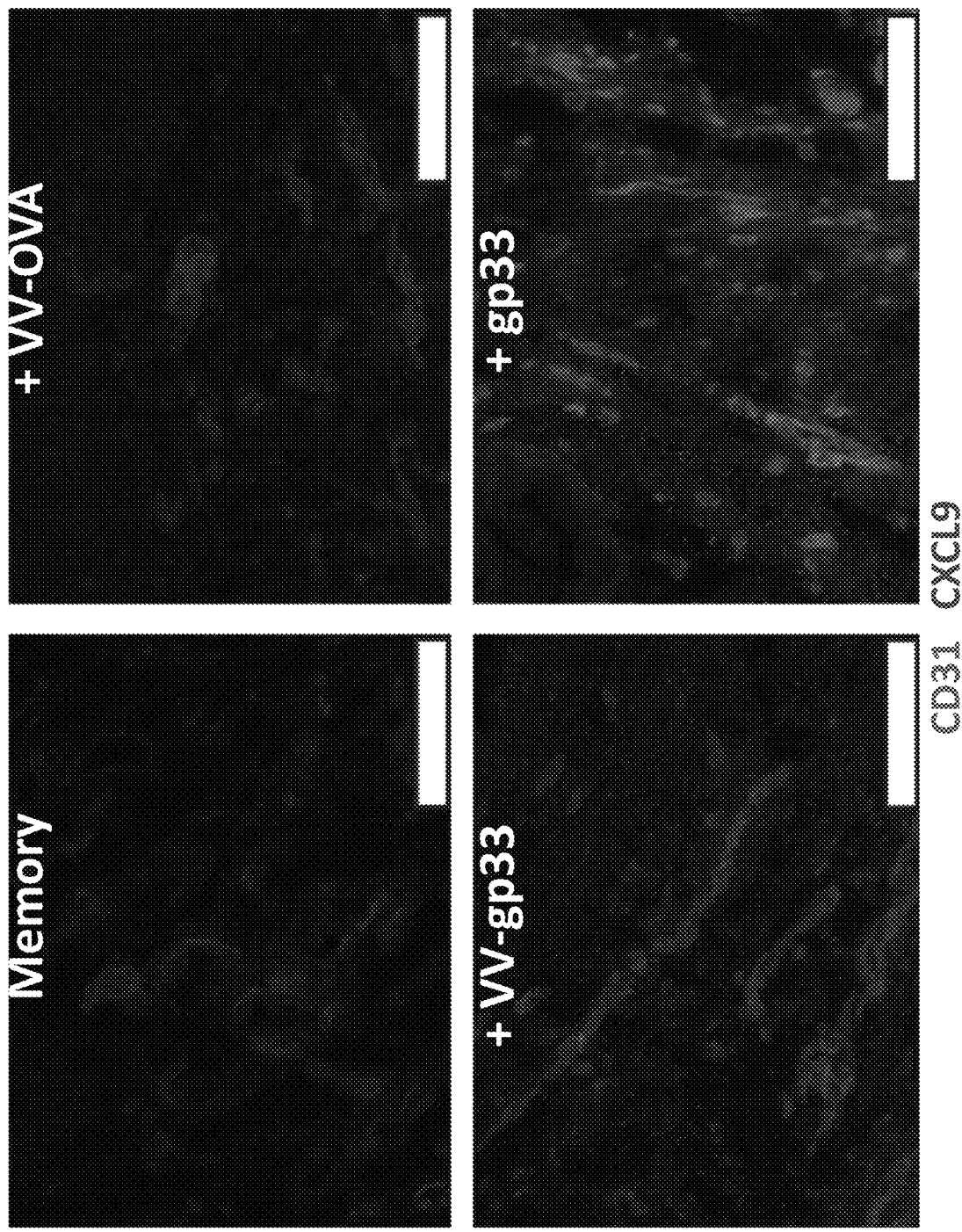
FIG. 3 are photographs showing that peptide reactivation of $T_{RM}$ triggers the production of chemokines.

Example 3—Chemokine Production Following the Reactivation of Resident Memory T Cells FIG. 3 are photographs showing that peptide reactivation of $T_{RM}$ triggers the production of chemokines. Mice were infected with lymphocytic choriomeningitis virus (LCMV), which resulted in the establishment of LCMV-specific $T_{RM}$ within many tissues, including the female reproductive tract. Gp33 is an immunodominant peptide from LCMV.

In the resting state (top left), the female reproductive tract expresses little inflammatory chemokine. 50 µg of the indicated peptides (bottom right) or $4 \times 10^5$ pfu of VV-gp33 (bottom left) or VV-OVA (top right) was delivered transcervically by modified gel loading pipet in a volume of 35 µl, which induced the reactivation of $T_{RM}$. VV-gp33 is a recombinant vaccinia virus expressing the gp33 peptide that functions in the present system to reactivate the $T_{RM}$. For example, administration of VV-gp33 provides the antigenic peptides as well as the intrinsic inflammatory cues resulting from the viral infection, whereas administration of VV-OVA provides the intrinsic inflammatory cues resulting from the viral infection but does not provide a peptide that is antigenic; thus, VV-OVA should not reactivate the $T_{RM}$.

12 h after local reactivation of LCMV-specific $T_{RM}$, chemokines were induced (CXCL9 is shown in FIG. 3; CXCL10, fractalkine, CCL2, CCL3/4, and CCL5 also were upregulated). This process was critically dependent on the presence of $T_{RM}$ and local antigen exposure, and exposure to a peptide (e.g., gp33) that was recognized by pre-existing $T_{RM}$ was particularly effective at inducing local chemokines (bottom right). In other words, administration of peptide that reactivates $T_{RM}$ was sufficient to induce this local chemokine response, and no additional adjuvants were required. These experiments demonstrate that the inflammatory cues that are intrinsic to the viral infection are not sufficient to induce chemokine production, and that it is the specific antigen peptide, gp33, that is recognized by gp33-specific $T_{RM}$ that induce chemokines. See also, for example, Schenkel et al. (2013, Nat. Immunol., 14(5):509-14).

Figure 4:
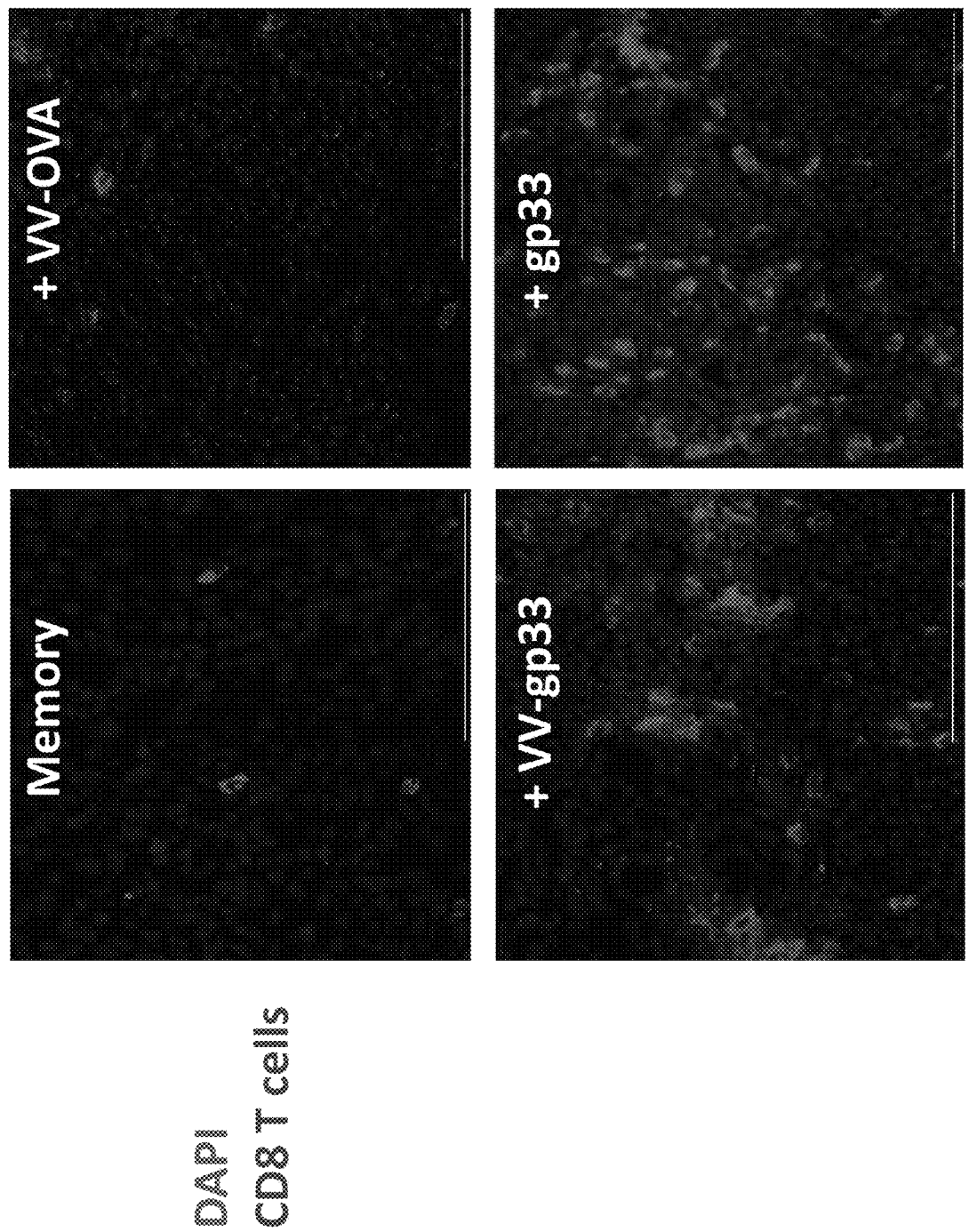
FIG. 4 are photographs showing that cells in a resting state have few CD8 T cells (top left) and that, when viral infection occurs in the absence of a suitable antigenic peptide, the number of CD8 T cells does not change, indicating no activation of $T_{RM}$ (top right).
Figure 5:
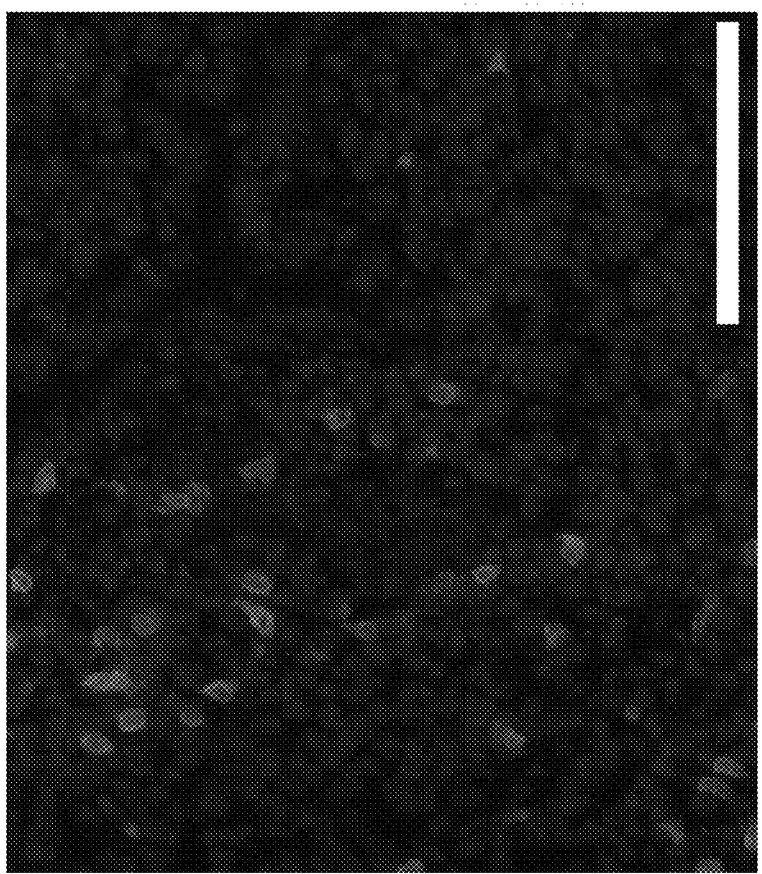
FIG. 5 are photographs showing that memory T cells that are specific for a particular antigenic peptide in the blood are recruited and activate $T_{RM}$ when a suitable antigenic peptide is provided (left panel) versus mice not given the antigenic peptide (right panel).
Figure 5:
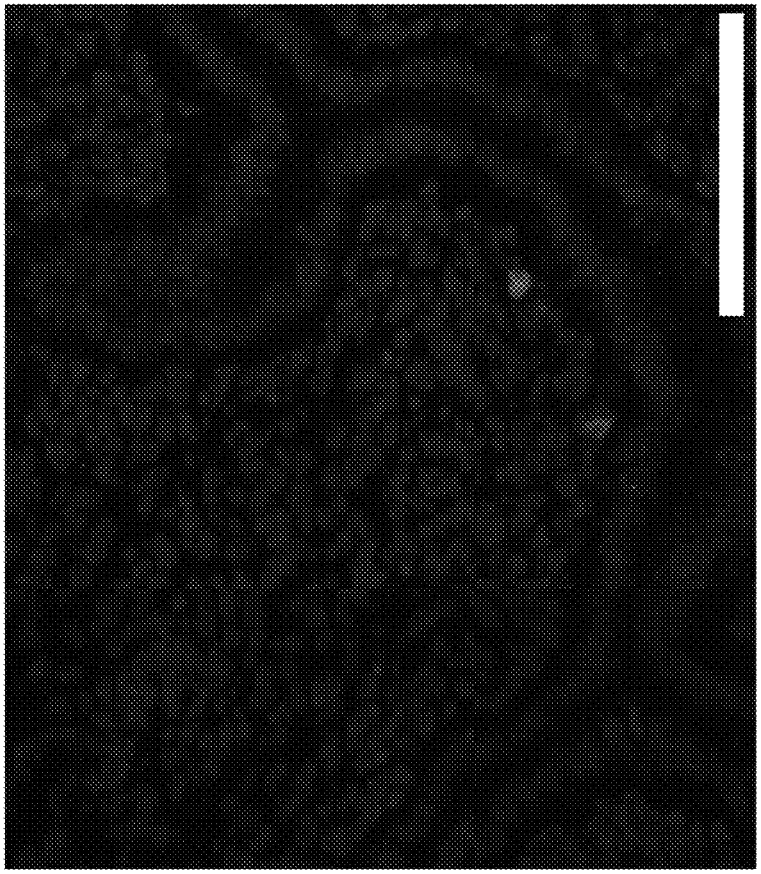

Examples 4—Leukocyte Recruitment Following the Reactivation of Resident Memory T Cells FIGS. 4 and 5 are photographs showing that peptide reactivation of $T_{RM}$ triggers leukocyte recruitment. 50 µg of the indicated peptides or $4 \times 10^5$ pfu VV-gp33 or VV-OVA was delivered transcervically to LCMV-immune mice by modified gel loading pipet in a volume of 35 µl, which induced the reactivation of $T_{RM}$. 48 h after local reactivation of LCMV-specific $T_{RM}$, LCMV-specific (FIG. 4, LCMV-specific CD8 T cells are in red) and LCMV non-specific (FIG. 5, non-specific "OT-I" CD8 T cells are in red) resting T cells migrated into the female reproductive tract. Other leukocytes also were recruited to sites of peptide-mediated $T_{RM}$ reactivation, including inflammatory monocytes and B cells.

FIG. 4 shows cells in a resting state, with few CD8 T cells in the tissue (top left). When viral infection occurs in the absence of a suitable antigenic peptide, the number of CD8 T cells does not change, indicating no activation of $T_{RM}$ (top right). When viral infection occurs in the presence of a suitable antigenic peptide, a significant number of CD8 T cells migrated into the tissue, indicating activation of $T_{RM}$ (bottom left). A suitable antigenic peptide alone in the absence of viral infection also recruits CD8 T cells (bottom right).

FIG. 5 shows that memory T cells that are specific for a particular antigenic peptide (Ova/OTI) in the blood are recruited when a suitable antigenic peptide (e.g., gp33) that activates $T_{RM}$ is provided (right panel). Left panel shows mice not given gp33 peptide. In summary, peptides that activate $T_{RM}$ induce potent recruitment of antigen-experienced T cells to the site of application.

See also, for example, Schenkel et al. (2013, Nat. Immunol., 14(5):509-14).

Figure 6:
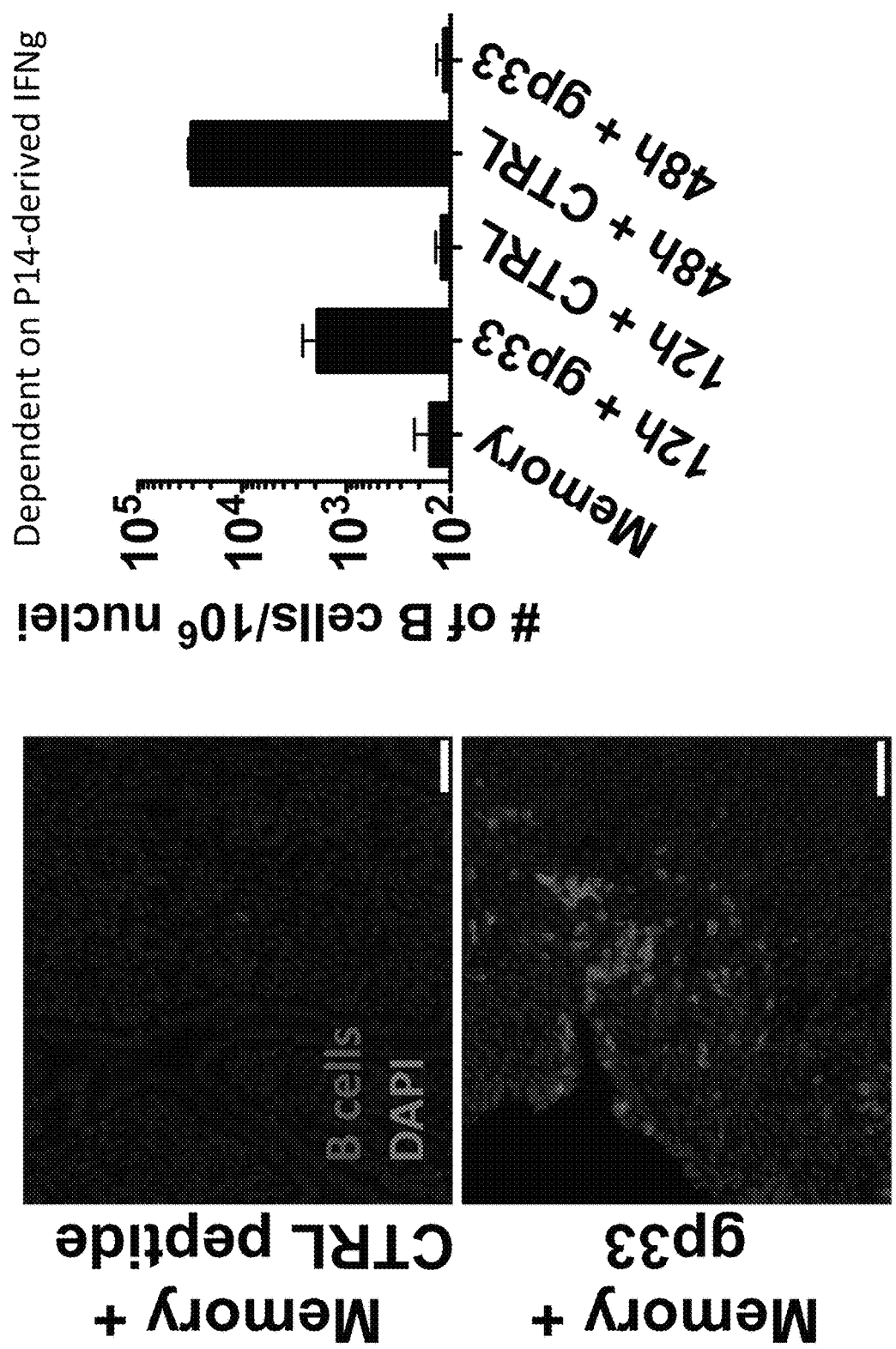
FIG. 6 is data showing that peptide reactivation of $T_{RM}$ triggers B cell recruitment.

Example 5—B Cell Recruitment Following the Reactivation of Resident Memory T Cells FIG. 6 is experimental data showing that peptide reactivation of $T_{RM}$ triggers B cell recruitment. 50 µg of gp33 or control peptide (the mouse does not have $T_{RM}$ specific for the control peptide, in this case SIINFEKL) was delivered transcervically to LCMV-immune mice by modified gel loading pipet in a volume of 35 µl, which induced the reactivation of $T_{RM}$. B cells were enumerated in the female reproductive tract 12 and 48 h later. See also, for example, Schenkel et al. (2014, Science, 346(6205):98-101).

Figure 7:
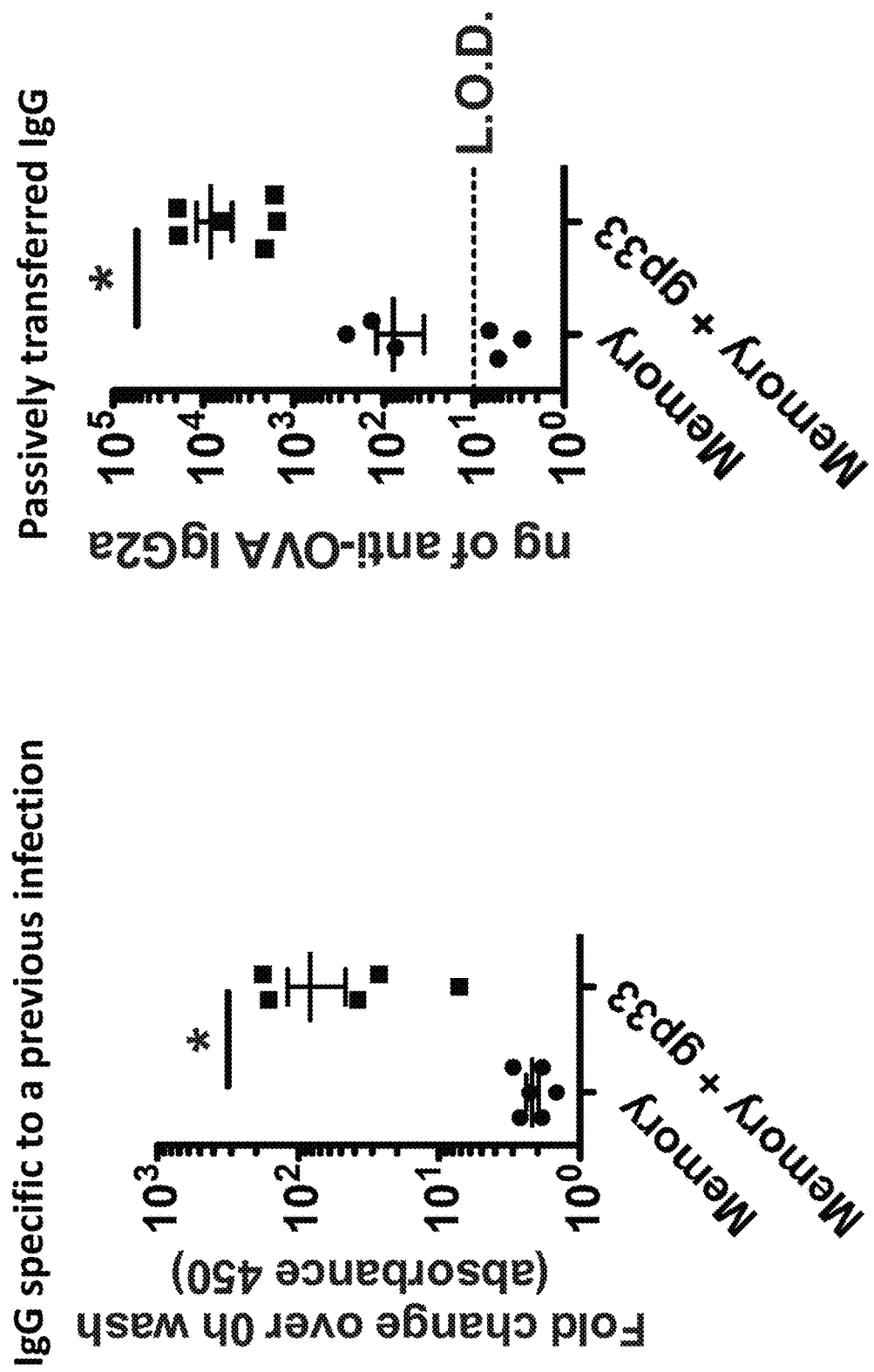
FIG. 7 are graphs showing that peptide reactivation of $T_{RM}$ triggers serum antibody recruitment.

Example 6—Serum Antibody Recruitment Following the Reactivation of Resident Memory T Cells FIG. 7 are graphs showing that peptide reactivation of $T_{RM}$ triggers serum antibody recruitment. Mice were infected with vesicular stomatitis virus (VSV). 30 days later, mice were infected with LCMV. Another 30 days later, 50 µg of gp33 was delivered transcervically by modified gel loading pipet in a volume of 35 µl, which induced the reactivation of LCMV-specific $T_{RM}$. VSV-specific IgG from serum was quantified in the mucosal lumen (left graph), and passively-transferred (i.v.) IgG was quantitated within the reproductive mucosa before and after $T_{RM}$ reactivation by the peptides (right graph). In summary, reactivation of $T_{RM}$ induced an increase in serum antibody, whether by active or passive transport, at the site of application.

Example 7—Reactivation of Resident Memory T Cells Recruits CAR-T Cells

Figure 8:
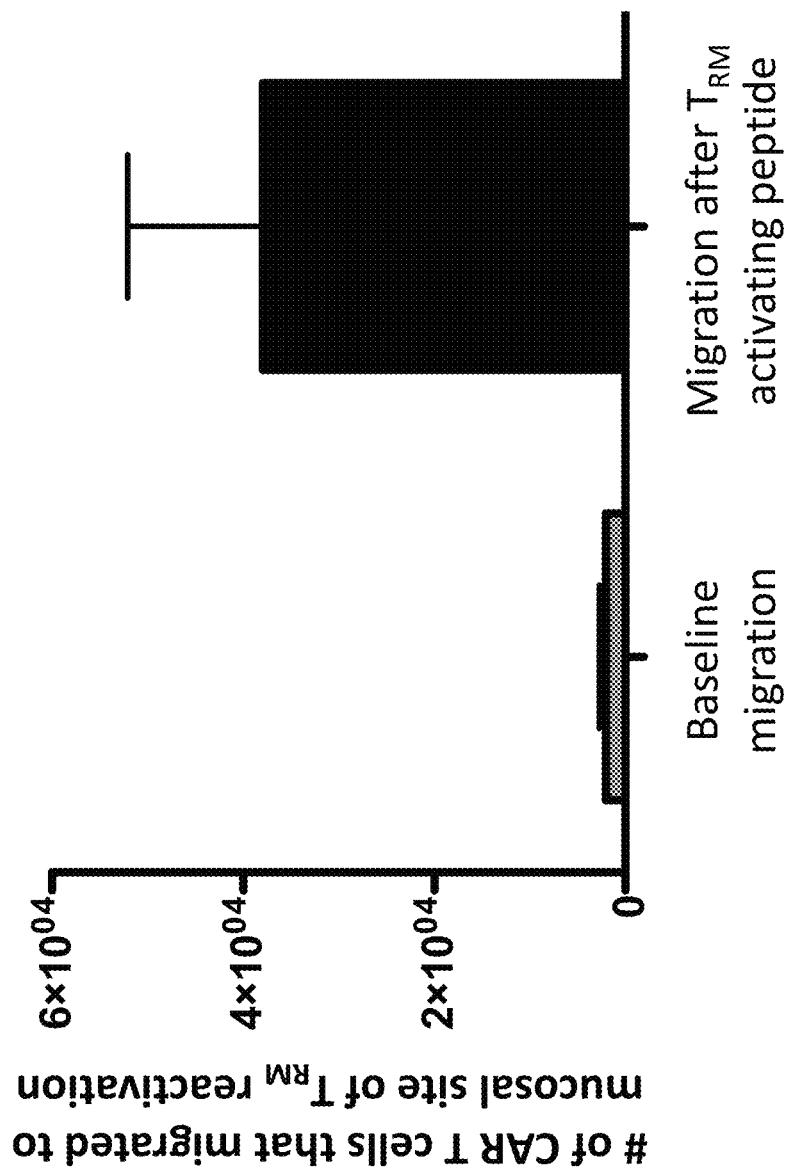
FIG. 8 is a graph demonstrating that peptide reactivation of $T_{RM}$ can be exploited to recruit CAR-T cells.

FIG. 8 is a graph demonstrating that peptide reactivation of $T_{RM}$ can be exploited to recruit CAR-T cells. Mice were infected with LCMV to establish $T_{RM}$ in a number of tissues. 60 days later, chimeric antigen receptor (CAR)-T cells were expanded in vitro and transferred into the mice intravenously. The following day, half of the mice received the gp33 peptide transcervically to induce the local reactivation of LCMV-specific $T_{RM}$, while the other half of the mice received no peptide treatment. CAR-T cell migration to reproductive tract was enumerated 48 h later. When the $T_{RM}$ are not reactivated (left bar), there was little migration of CAR-T cells into the tissue. After the gp33 peptide was administered (right bar), the number of CAR-T cells in the female reproductive tract increases 19-fold. In other words, 19-times more CAR-T cells were present in the tissue following administration of the antigenic peptides and reactivation of the $T_{RM}$ as described herein than were present in the absence of the antigenic polypeptide.

Figure 9:
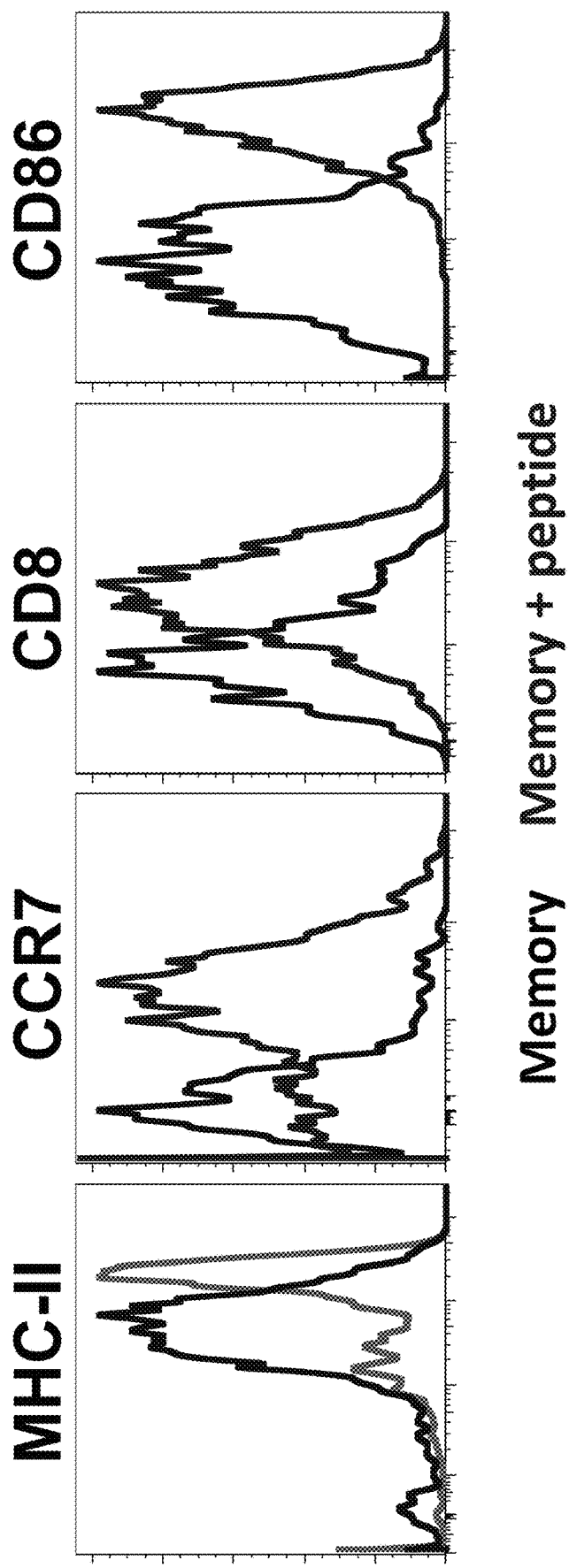
FIG. 9 is data showing that peptide reactivation of $T_{RM}$ triggers local dendritic cell activation.

Example 8—Reactivation of Resident Memory T Cells Triggers Local Dendritic Cell Activation FIG. 9 is data showing that peptide reactivation of $T_{RM}$ triggers local dendritic cell activation. 50 µg of gp33 was delivered transcervically by modified gel loading pipet to LCMV-immune mice in a volume of 35 which induced the reactivation of $T_{RM}$. 12 h later, dendritic cells were isolated from the reproductive tract and measured by flow cytometry for expression of MHC II, CCR7, and co-stimulatory molecules, CD80 and CD86. See also, for example, Schenkel et al. (2014, Science, 346(6205):98-101).

Figure 10:
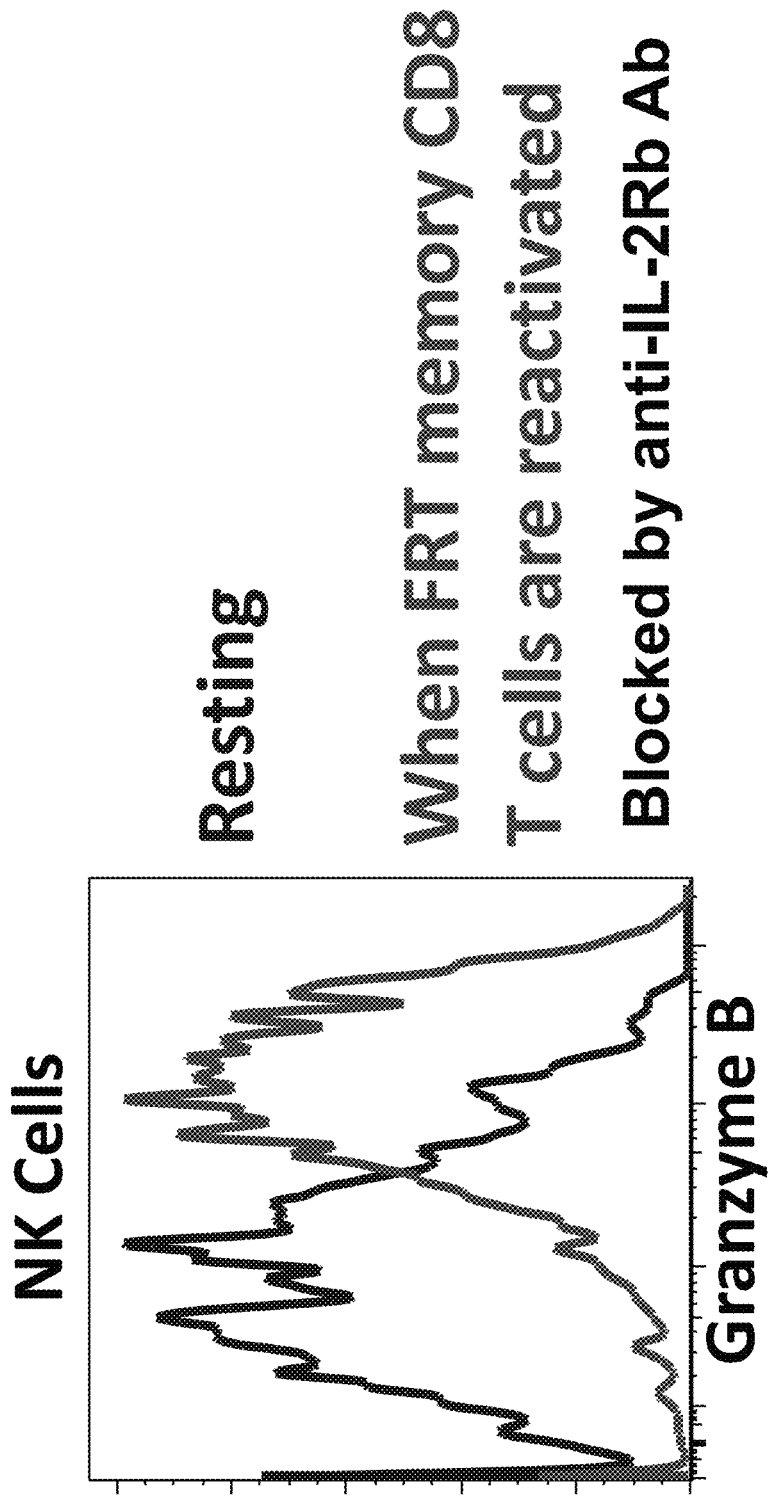
FIG. 10 is data showing that peptide reactivation of $T_{RM}$ triggers local natural killer (NK) cell activation.

Example 9—Reactivation of Resident Memory T Cells Triggers Local Natural Killer Cell Activation FIG. 10 is data showing that peptide reactivation of $T_{RM}$ triggers local natural killer (NK) cell activation. 50 µg of gp33 was delivered transcervically by modified gel loading pipet to LCMV immune mice in a volume of 35 which induced the reactivation of $T_{RM}$. 12 h later, NK cells were isolated from the reproductive tract and measured by flow cytometry for expression of granzyme B. See also, for example, Schenkel et al. (2014, Science, 346(6205):98-101).

Example 10—Summary of the Function of Resident Memory T Cells

Figure 11:
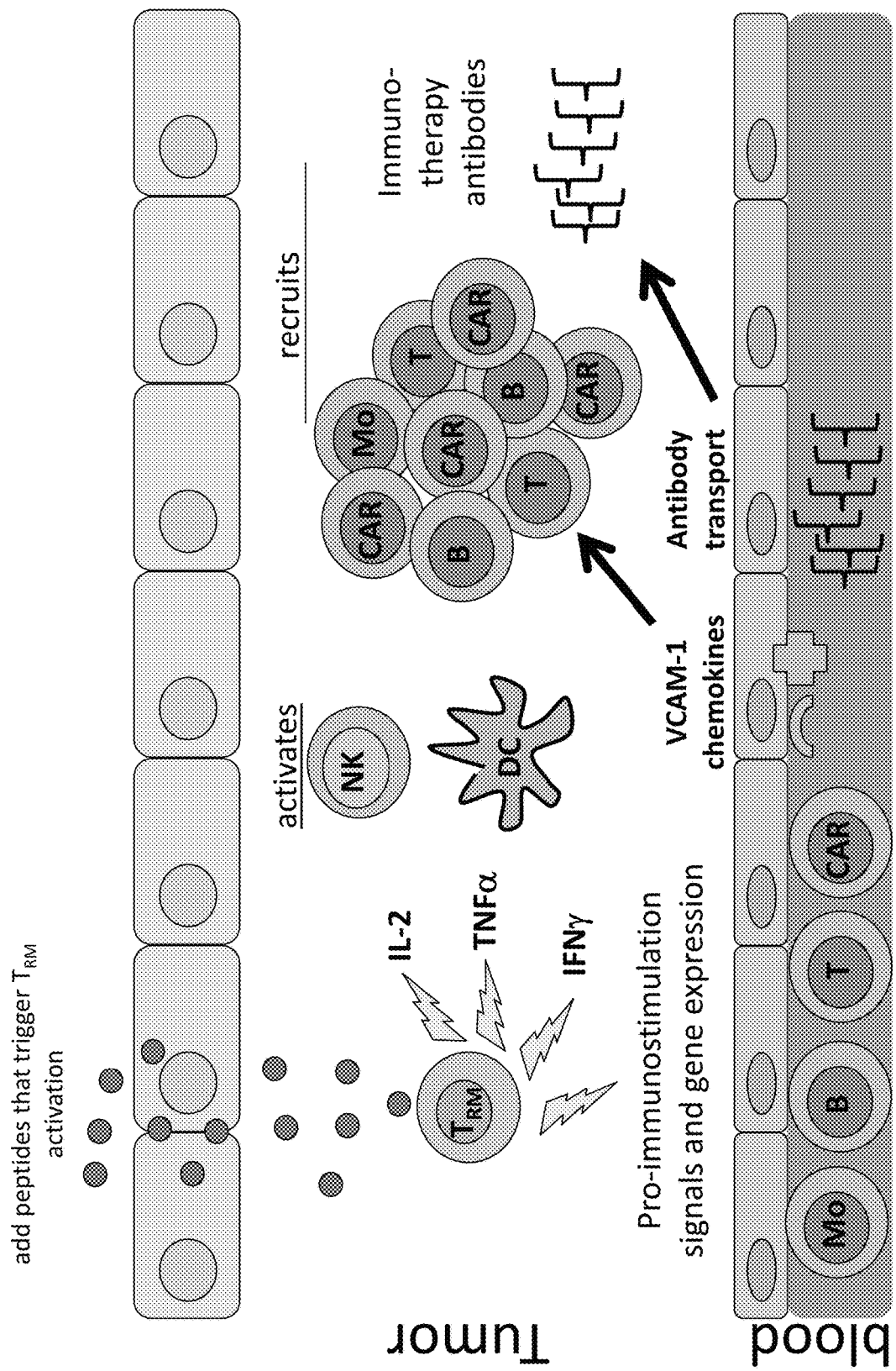
FIG. 11 provides a summary of the sensing and alarm function of $T_{RM}$.

FIG. 11 provides a summary of the sensing and alarm function of $T_{RM}$. When $T_{RM}$, established during a prior immunological event (e.g., a vaccination or an infection), encounter their cognate peptide in tissue through a topical application, they precipitate a number of local changes in the immunological environment. For example, peptide-reactivated $T_{RM}$ trigger the production of chemokines and the upregulation of vascular adhesion molecules, including VCAM-1, which induces the recruitment of various leukocytes and serum antibody and promotes a local immunostimulatory environment.

Example 11—Summary of Experiments Using gp33

The peptide used herein, gp33, was particularly effective at inducing local $T_{RM}$ reactivation. While peptide dose was defined empirically, it was demonstrated that local peptide administration was effective over a 1000-fold titration. The peptide can be delivered in saline, or can be mixed with carriers to promote prolonged or optimized in vivo presentation.

Example 12—Skin Tumors Are Populated by Resident Memory T Cells

Figure 12:
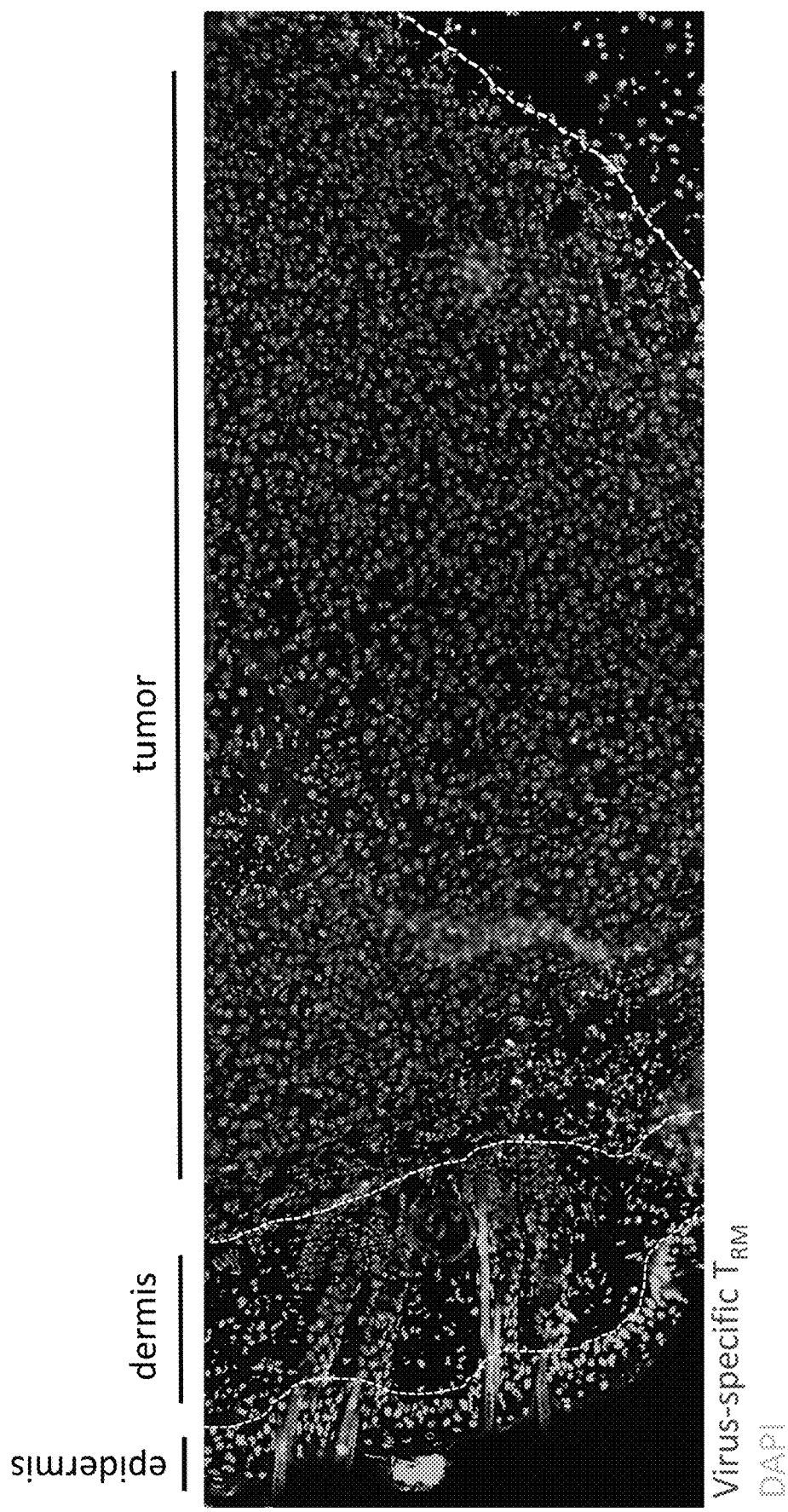
FIG. 12 is a photograph showing that virus-specific Trm populates skin tumor.

FIG. 12 is a photograph showing that virus-specific $T_{RM}$ populates skin tumor. Mice were infected with vesicular stomatitis virus (VSV) i.v., which is cleared from mice within less than a week after infection. This establishes $T_{RM}$ in many tissues, including skin (data not shown). In this example, mice were injected i.d. with the B16 melanoma cell line 45 days after VSV infection. As shown in FIG. 12, VSV-specific $T_{RM}$ became integrated within tumor microenvironment (image shown is 15 days after B16 implantation).

Example 13—Reactivation of Resident Memory T Cells in Skin Tumors

Figure 13:
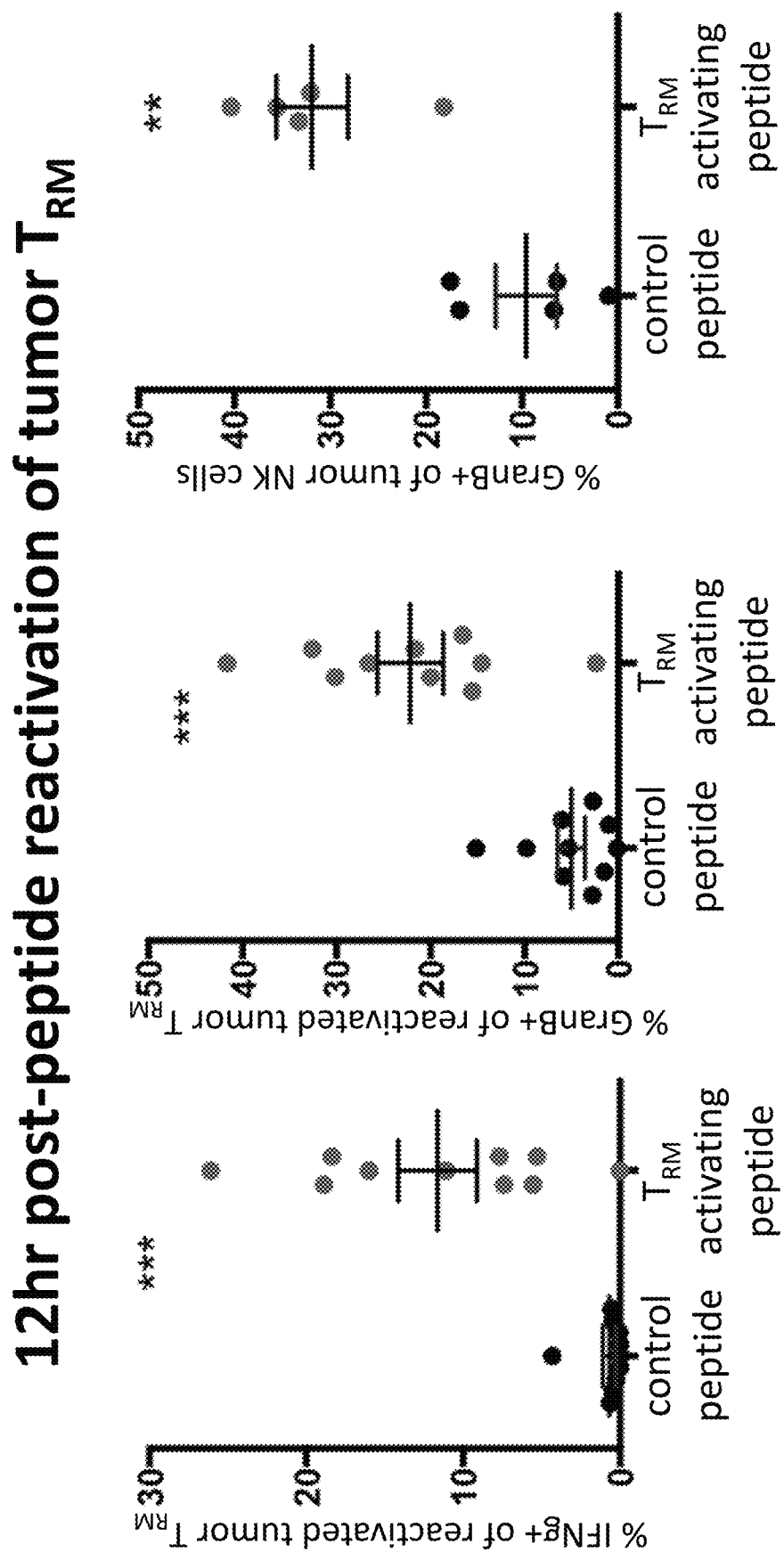
FIG. 13 are graphs showing that virus-specific Trm within skin tumors can become reactivated.

FIG. 13 are graphs showing that virus-specific $T_{RM}$ within skin tumors can become reactivated by the presence of an antigenic peptide. Mice were infected with VSV-Ova (recombinant VSV expressing ovalbumin) i.v. 45 days later, mice were injected i.d. with the B16 melanoma cell line (which does not express ovalbumin). 15 days after B16 implantation, this site was tattooed with VSV-Ova derived peptides (SIINFEKL), and VSV-Ova specific $T_{RM}$ and NK cells isolated from the tumor were examined 12 h later by flow cytometry.

Example 14—Functional Analysis of Reactivated Resident Memory T Cells

Figure 14:
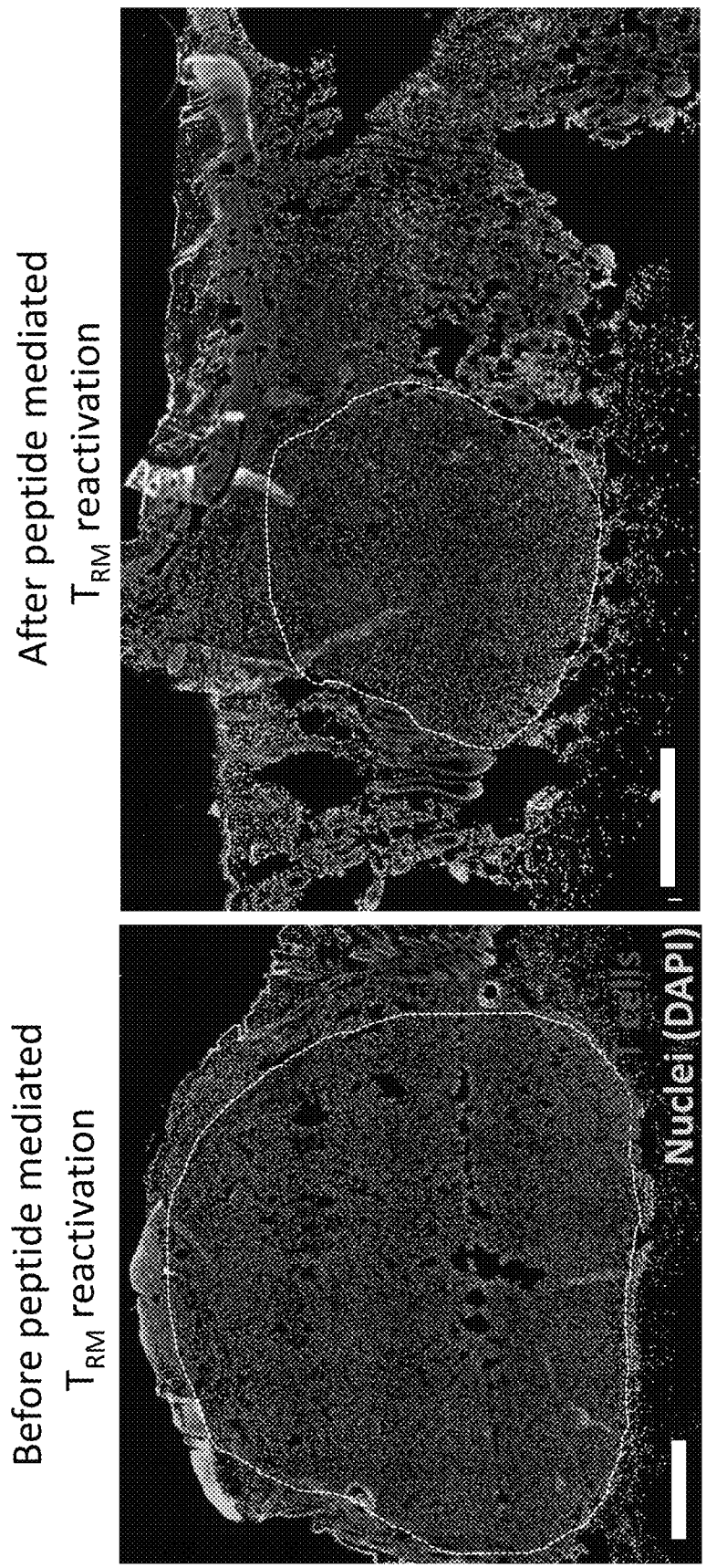
FIG. 14 are photographs showing that virus-specific Trm within skin tumors recruit CD8 T cells and NK cells to tumors after reactivation.

FIG. 14 are photographs showing that virus-specific $T_{RM}$ within skin tumors recruit CD8 T cells and NK cells to the tumors after being reactivated with an antigenic peptide. Mice were infected with VSV-Ova i.v. and 45 days later, mice were injected i.d. with the B16 melanoma cell line (which does not express Ova). 15 days after B16 implantation, the site was tattooed with VSV-Ova derived peptides and stained 48 h later with anti-CD8a antibodies (red) or for NK cells (data not shown).

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of increasing the efficacy of immunotherapy in an individual, comprising administering an adjuvant to a solid tumor, wherein the adjuvant comprises at least two antigenic peptides from one or more viruses or bacteria against which the individual previously has been inoculated and developed an immune response, wherein the one or more viruses or bacteria are selected from the group consisting of varicella-zoster virus (VZV)), polio, *Rubella* spp., mumps, Diphtheria, and *Clostridium tetani*.

2. The method of claim 1, wherein the one or more viruses or bacteria against which the individual has previously developed an immune response are pathogenic or infectious.

3. The method of claim 1, wherein the adjuvant comprises at least three antigenic peptides from one or more viruses or bacteria.

4. The method of claim 1, wherein the administering is intratumorally.

5. The method of claim 4, wherein the intratumoral administering is via injection.

6. The method of claim 1, wherein the adjuvant further comprises a pharmaceutically acceptable carrier.

7. The method of claim 6, wherein the pharmaceutically acceptable carrier is saline.

8. The method of claim 1, further comprising a second administering step.

9. A method of increasing the efficacy of immunotherapy in an individual, comprising administering an adjuvant to a solid tumor, wherein the adjuvant comprises at least one antigenic peptides from EBV and at least one antigenic peptides from CMV.

10. The method of claim 9, wherein the adjuvant comprises at least two antigenic peptides from EBV.

11. The method of claim 9, wherein the adjuvant comprises at least two antigenic peptides from CMV.

12. The method of claim 9, further comprising a pharmaceutically acceptable carrier.

13. The method of claim 12, wherein the pharmaceutically acceptable carrier is saline.

14. A method of increasing the efficacy of immunotherapy in an individual, comprising administering the immunotherapy to the individual, wherein the improvement comprises administering an adjuvant to a tumor, wherein the adjuvant comprises at least two antigenic peptides from one or more viruses or bacteria, wherein the one or more viruses are selected from the group consisting of EBV and CMV.

15. An article of manufacture comprising:
   at least one an antigenic peptide from a first microorganism;
   at least one an antigenic peptide from a second microorganism; and
   a pharmaceutically acceptable carrier,
wherein the first microorganism is EBV and wherein the second microorganism is CMV.

16. The method of claim 1, wherein the one or more viruses or bacteria against which the individual has previously developed an immune response are pathogenic or infectious.

17. The method of claim 1, wherein the adjuvant comprises at least three antigenic peptides from the one or more viruses or bacteria.

18. The method of claim 1, wherein the administering is intratumorally.

19. The method of claim 18, wherein the intratumoral administering is via injection.

20. The method of claim 1, wherein the adjuvant further comprises a pharmaceutically acceptable carrier.

21. The method of claim 20, wherein the pharmaceutically acceptable carrier is saline.

22. The method of claim 1, further comprising a second administering step.

* * * * *

UNITED STATES PATENT AND TRADEMARK OFFICE
CERTIFICATE OF CORRECTION

| | | |
|---|---|---|
| PATENT NO. | : 11,642,401 B2 | |
| APPLICATION NO. | : 16/939962 | |
| DATED | : May 9, 2023 | |
| INVENTOR(S) | : David B. Masopust, Jr. and Vaiva D. Vezys | |

It is certified that error appears in the above-identified patent and that said Letters Patent is hereby corrected as shown below:

On the Title Page

Item (56), References Cited, OTHER PUBLICATIONS, Line 2, please delete "xenotrausplanted" and insert therefor -- xenotransplanted --;

Item (56), References Cited, OTHER PUBLICATIONS, Line 20, please delete "-mfo/hl-" and insert therefor -- -info/hla- --; and In the Claims Column 11, Claim 1, Line 55, please delete "(VCV))," and insert therefor -- (VZV), --.

Signed and Sealed this
First Day of October, 2024

*Katherine Kelly Vidal*

Katherine Kelly Vidal
*Director of the United States Patent and Trademark Office*